(12) United States Patent
Hamm et al.

(10) Patent No.: US 6,420,416 B2
(45) Date of Patent: Jul. 16, 2002

(54) METHOD OF TREATING EPILEPSY

(75) Inventors: Robert Hamm, Crozier; S. Michelle Deford, Richmond, both of VA (US); Tadashi Shiotani, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/886,206

(22) Filed: Jun. 22, 2001

Related U.S. Application Data

(62) Division of application No. 09/547,226, filed on Apr. 11, 2000.

(51) Int. Cl.$^7$ .............................................. A61K 31/40
(52) U.S. Cl. ...................................................... 514/424
(58) Field of Search ......................................... 514/424

(56) References Cited

U.S. PATENT DOCUMENTS

| | | | |
|---|---|---|---|
| 5,461,157 A | 10/1995 | Kamihara et al. | |
| 5,886,023 A | 3/1999 | Otomo et al. | |
| 6,107,330 A | 8/2000 | Nabeshima et al. | |

FOREIGN PATENT DOCUMENTS

| WO | WO 00/07593 | 2/2000 |
|---|---|---|

OTHER PUBLICATIONS

Berlow (ed.), The Merck Manual, Published by Merck & Company (NJ), pp. 1305–1307) (1982).

Abstract from the 17$^{th}$ annual meeting of the Japan Neuroscience Society, Nagoya, Japan, Dec. 7–9, 1993, 2 pp.

Brian R. Pike, et al., "Effect of Tetrahydroaminoacridine, a Cholinesterase Inhibitor, on Cognitive Performance Following Experimental Brain Injury", Journal of Neurotrauma, vol. 14, No. 12, pp. 897–905, 1997.

Kiyofumi Yamada, et al., "Nefiracetam (DM–9384): A Novel Antiamnesic Drug", CNS Drug Reviews, vol. 2, No. 3, pp. 322–342, 1996.

Robert J. Hamm, et al., "Cognitive impairment following traumatic brain injury: the effect of pre– and post–injury administration of scopolamine and MK–801", Cognitive Brain Research, vol. 1, pp. 223–226, 1993.

B.G. Lyeth, et al., "Effects of scopolamine treatment on long–term behavioral deficits following concussive brain injury to the rat", Brain Research, vol. 452, pp. 39–48, 1988.

*Primary Examiner*—Raymond Henley, III
(74) *Attorney, Agent, or Firm*—Oblon, Spivak, McClelland, Maier & Neustadt, P.C.

(57) ABSTRACT

A method for treatment of neuronal disorders and traumatic brain injury is provided which involves timely administration to a subject in need thereof of an effective amount of nefiracetam.

5 Claims, 1 Drawing Sheet

METHOD OF TREATING EPILEPSY

This is a divisional of U.S. patent application Ser. No. 09/547,226 filed Apr. 11. 2000.

BACKGROUND OF THE INVENTION

1. Field of the Invention

The present invention relates to a method for treatment of brain injury and neuronal disorders, such as epilepsy, by administration of an effective amount of nefiracetam.

2. Discussion of the Background

Traumatic brain injury, as well as neuronal disorders with common pathological features, such as stroke and epilepsy, can have devastating effects on a person, both short-term and long-term. Traumatic brain injury is often associated with cerebral concussion. Cerebral concussion is a traumatically induced derangement of the nervous system, characterized clinically by immediate and transient impairment of consciousness and is generally not associated with remarkable gross anatomical changes. Even moderate levels of concussive human head injury, not requiring prolonged hospitalization, can result in persistent neurological disturbances often lasting for months. These disturbances often include dizziness and balance problems, and fine motor skill dysfunction. Lyeth et al, *Brain Research,* 452, 39–48 (1988).

Traumatic brain injury is known to be a biphasic process. The first phase, the excitatory phase, occurs immediately upon injury. During this phase there is great neuronal excitation due to the trauma. Following the excitatory phase is the recovery phase, during which the neuronal excitation has abated and the job of repair has begun. Most often with traumatic brain injury, the excitatory phase is associated with increased intracranial pressure (ICP), with fluctuations of ICP over several days or more. Patients in the excitatory phase must typically be cared for in the intensive care unit of a hospital. Once the ICP has been stabilized and the patient can be removed from intensive care, the patient is typically entering into the recovery phase.

Traumatic brain injury produces an acute neuronal depolarization and an extensive release of neurotransmitters. The resulting excessive receptor activation may produce abnormal neurotransmitter-receptor interactions which contribute to the pathophysiology associated with experimental traumatic brain injury. Both the cholinergic and glutamatergic receptor systems have been documented to play a prominent role in the receptor-mediated pathophysiology of traumatic brain injury. Prior attempts to treat traumatic brain injury have focused on administration of antagonists of these cholinergic or glutamatergic receptors (such as the AMPA-glutamate receptor, wherein AMPA represents α-amino-3-hydroxy-5-methyl-4-isoxazole propionic acid) as early as possible after the occurrence of the injury. (See Hamm et al, *Cognitive Brain Research,* 1, 223–226 (1993) and Lyeth et al, *Brain Research,* 452, 39–48 (1988)). The goal of these studies was to add the antagonist during the excitatory phase of the injury process during the period of high receptor activity in an attempt to minimize the damage occurring to the neuronal tissue. Unfortunately, such attempts were not successful.

SUMMARY OF THE INVENTION

Accordingly, one object of the present invention is to provide a method effective for the treatment of brain injuries, particularly traumatic brain injury.

A further object of the present invention is to provide a method for treatment of neuronal disorders such as epilepsy.

These and other objects of the present invention have been satisfied by the discovery of a method for the treatment of neuronal disorders and brain injury comprising:

administering to a subject in need thereof, an effective amount of nefiracetam.

DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
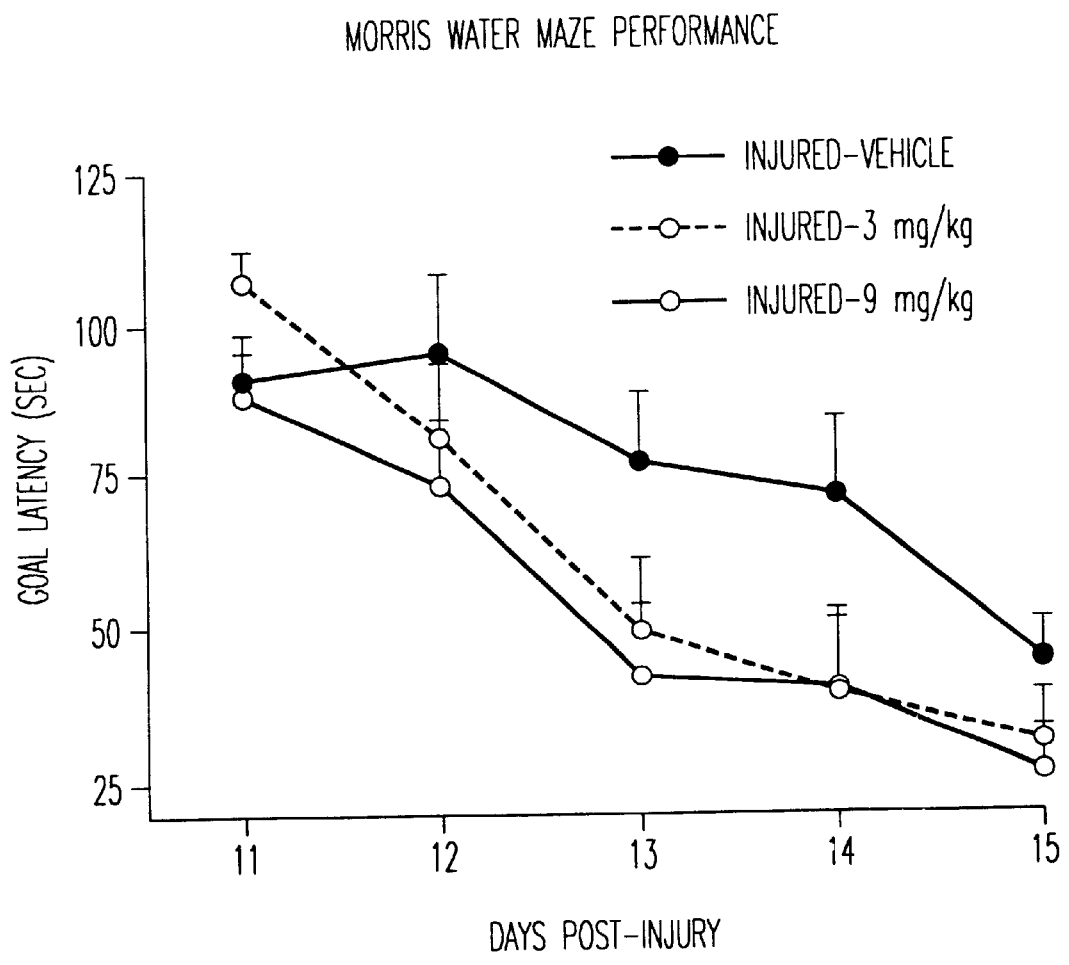
FIG. 1 is a graphical presentation of test data on brain injured rats showing the improvement in performance achieved using the present method compared to a control group.

The present invention relates to a method for the treatment of neuronal disorders and brain injury which comprises administering to a subject in need thereof, an effective amount of nefiracetam.

The present inventors have found that administration of nefiracetam to a subject that has suffered a neuronal disorder or a traumatic brain injury, can provide dramatic improvements in brain function. An important factor in the present method is to administer nefiracetam as soon as possible after the excitatory phase of the injury process has ceased and the patient has entered into the recovery phase. If nefiracetam is administered too early, during the excitatory phase, the injury to the patient can actually be increased. However, if nefiracetam is administered during the period between entry into the recovery phase and the time at which the injury becomes permanent, the administration of nefiracetam can be highly effective at improving the recovery process and restoring significant levels of brain function.

The present method can use nefiracetam or one or more of its metabolites. Within the context of the present text, use of the term nefiracetam includes the possible use of one or more metabolites. Of course, the metabolites will have different chemical structures and different dosage levels, which are easily determinable by those of skill in the art. Nefiracetam (N-(2,6-dimethyl-phenyl)-2(2-oxo-1-pyrrolidinyl)acetamide) is a drug having the structure:

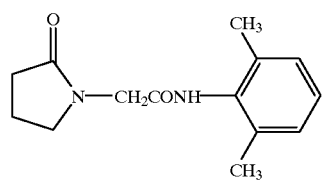

It has previously been used as a nootropic drug in the treatment of senile dementia and Alzheimer's disease. An excellent review of the use of nefiracetam in such treatment is found in Yamada et al, *CNS Drug Reviews,* 2, 322–342 (1996), which is hereby incorporated by reference.

The nefiracetam can be administered neat or as a composition comprising nefiracetam and a pharmacologically acceptable carrier. Suitable carriers include water, saline and other conventionally used pharmacological carriers. The composition comprises from 0.1 to 100% of nefiracetam. The concentration of nefiracetam in the composition can be adjusted as desired to achieve a manageable dosage volume to provide any desired non-lethal dosage, preferably from 1 mg/kg to 30 mg/kg, more preferably from 5 mg/kg to 15 mg/kg, most preferably about 9 mg/kg per oral. Alternatively, nefiracetam can be administered in any orally or IV administrable form, such as tablets, troches, powders, emulsions, solutions, etc.

The administration of nefiracetam should preferably begin as quickly as possible after the patient enters the recovery phase of the injury process or as soon as possible after the neuronal disorder is detected. Ideally, administration should begin no later than 1.5–2 weeks after entry into the recovery phase, most preferably no later than 1 week after entry into the recovery phase. The excitatory phase is characterized most often by fluctuations in ICP, during which the patient is typically placed in the intensive care unit of a hospital. Once the ICP has stabilized and the patient can be moved from the intensive care unit, the recovery phase is considered to be entered.

Preferably, the composition should be administered daily, with from 1 to 4 dosages per day. Improvements can typically be seen in the subject's brain function within about 2 weeks, although longer treatments can provide further improvement. Chronic administration, even up to lifetime administration, can be performed if desired.

FIG. 1, shows the results achieved in rats using the method of the present invention. As shown in the graph, administration of nefiracetam at 3 mg/kg and 9 mg/kg were tested against a control group treated only with the pharmacological carrier (9% saline). The rats were subjected to a central fluid percussion injury, which is a typical animal model for traumatic brain injury. Beginning one day after the injury, the rats were subjected to daily oral drug administrations at the 3 and 9 mg/kg dosage levels. The administration solutions contained the nefiracetam in 9% saline at a concentration sufficient to provide the required dosage level in a single 1 ml/kg dosage of solution. The rats were then tested in the Morris water maze on days 11–15 after injury. On the days that the rats were tested, the drug was administered 15 minutes prior to testing. The rats at the 9 mg/kg dosage level shows significant improvement in brain finction as measured by performance in the water maze as compared to the control and the 3 mg/kg dosage level rats. The improvement seen at the 9 mg/kg dosage correlates to a reduction in the cognitive deficit by 55% compared to the control. The 3 mg/kg dosage level was not significantly effective.

What is claimed is:

1. A method for the treatment of epilepsy comprising:
   administering to a subject in need thereof, an effective amount of nefiracetam or a metabolite thereof.

2. The method of claim 1, wherein said effective amount of nefiracetam or a metabolite thereof is in the range of from 1 mg/kg to 30 mg/kg.

3. The method of claim 2, wherein said effective amount of nefiracetam or a metabolite thereof is in the range of from 5 mg/kg to 15 mg/kg.

4. The method of claim 1, wherein nefiracetam is present in a composition comprising nefiracetam and a pharmacologically acceptable carrier.

5. The method of claim 1, wherein said administering step is conducted from 1 to 4 times per day.

* * * * *